(12) United States Patent
Ito et al.

(10) Patent No.: US 9,310,190 B2
(45) Date of Patent: Apr. 12, 2016

(54) SURFACE SHAPE MEASURING APPARATUS

(75) Inventors: Masaaki Ito, Tokyo (JP); Takahiro Jingu, Tokyo (JP); Hisashi Hatano, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 40 days.

(21) Appl. No.: 14/240,669

(22) PCT Filed: Jul. 27, 2012

(86) PCT No.: PCT/JP2012/069076
§ 371 (c)(1),
(2), (4) Date: Feb. 24, 2014

(87) PCT Pub. No.: WO2013/031445
PCT Pub. Date: Mar. 7, 2013

(65) Prior Publication Data
US 2014/0198321 A1    Jul. 17, 2014

(30) Foreign Application Priority Data

Aug. 31, 2011    (JP) .................................. 2011-188164

(51) Int. Cl.
*G01B 11/24*    (2006.01)
*G01N 21/55*    (2014.01)
(Continued)

(52) U.S. Cl.
CPC .............. *G01B 11/24* (2013.01); *G01B 11/303* (2013.01); *G01N 21/4738* (2013.01); *G01N 21/55* (2013.01); *G01B 2210/56* (2013.01); *G01N 21/9501* (2013.01)

(58) Field of Classification Search
CPC ...... G01B 11/24; G01B 11/303; G01N 21/55; G01N 21/95; G01N 21/4738

USPC .............. 356/237.1–241.6, 242.1–243.8, 356/426–431, 600–640
See application file for complete search history.

(56) References Cited

U.S. PATENT DOCUMENTS 4,806,774 A  *  2/1989  Lin et al. ...................... 250/550
4,846,578 A  *  7/1989  Morita ................. G01B 11/303
                                                          356/124.5

(Continued)

FOREIGN PATENT DOCUMENTS

JP    07-333164 A    12/1995
JP    09-503299    *  12/1995

(Continued)

OTHER PUBLICATIONS

English translation of Notification of Reasons for Refusal issued in Japanese Application No. 2011-188164 dated Apr. 8, 2014.

(Continued)

*Primary Examiner* — Tri Ton
*Assistant Examiner* — Jarreas C Underwood
(74) *Attorney, Agent, or Firm* — McDermott Will & Emery LLP (57) ABSTRACT

In related art, consideration is not given to that a spatial distribution of scattered light changes in various direction such as forward/backward/sideways according to a difference in micro roughness. Particularly, although a step-terrace structure appearing on an epitaxial growth wafer produces anisotropy in the scattered light distribution, consideration is not given to this point in the related art. The invention includes a process in which light is illuminated to a sample surface, plural detection optical systems mutually different in directions of optical axes detect a spatial distribution of scattered light, and a spatial frequency spectrum of the sample surface is calculated.

13 Claims, 6 Drawing Sheets

(51) Int. Cl.
*G01B 11/30* (2006.01)
*G01N 21/47* (2006.01)
*G01N 21/95* (2006.01)

(56) References Cited

U.S. PATENT DOCUMENTS

| | | | | |
|---|---|---|---|---|
| 5,428,442 | A * | 6/1995 | Lin | G02B 27/46 |
| | | | | 356/237.5 |
| 5,646,725 | A * | 7/1997 | Hagiwara | 356/237.4 |
| 5,877,860 | A * | 3/1999 | Borden | G01B 11/303 |
| | | | | 356/613 |
| 7,106,454 | B2 * | 9/2006 | De Groot | G01B 11/0675 |
| | | | | 356/497 |
| 7,184,139 | B2 * | 2/2007 | Treves | G01N 21/9506 |
| | | | | 356/237.2 |
| 7,286,218 | B2 * | 10/2007 | Tiemeyer | G01N 21/21 |
| | | | | 356/237.2 |
| 8,358,575 | B2 * | 1/2013 | Deliwala | 370/210 |
| 8,831,899 | B2 * | 9/2014 | Nemoto | G01N 21/9501 |
| | | | | 356/237.5 |

| | | | |
|---|---|---|---|
| 2004/0223214 | A1 | 11/2004 | Atkinson |

FOREIGN PATENT DOCUMENTS

| | | | |
|---|---|---|---|
| JP | 09-503299 | A | 3/1997 |
| JP | 2000-031224 | A | 1/2000 |
| JP | 2002-257518 | A | 9/2002 |
| JP | 2006278515 | A | 10/2006 |
| JP | 2007-500881 | * | 1/2007 |
| JP | 2007-500881 | A | 1/2007 |
| JP | 2008-058239 | A | 3/2008 |
| JP | 2008-278515 | A | 11/2008 |
| JP | 2010-223770 | A | 10/2010 |

OTHER PUBLICATIONS

International Search Report, w/ English translation thereof, issued in International Application No. PCT/JP2012/069076 dated Nov. 6, 2012.

* cited by examiner

SCATTERED LIGHT OF SPATIAL
FREQUENCY SPECTRUM S1

SCATTERED LIGHT OF SPATIAL
FREQUENCY SPECTRUM S2

SURFACE SHAPE MEASURING APPARATUS

RELATED APPLICATIONS

This application is the U.S. National Phase under 35 U.S.C. §371 of International Application No. PCT/JP2012/069076, filed on Jul. 27, 2012, which in turn claims the benefit of Japanese Application No. 2011-188164, filed on Aug. 31, 2011, the disclosures of which Applications are incorporated by reference herein.

TECHNICAL FIELD

The present invention relates to a surface shape measuring apparatus for obtaining a surface shape. For example, the invention relates to a surface shape measuring apparatus using light scattering, and particularly to a measuring apparatus of micro roughness of a wafer surface or the like in a semiconductor device manufacturing process.

BACKGROUND ART

As a semiconductor device is micronized, the influence of micro roughness of the surface of a bare wafer or a wafer with film on electrical characteristics increases. Since the micro roughness is produced in processes such as polishing, cleaning, film formation and heat treatment, in order to improve the performance and yield of a device, it is necessary to measure the micro roughness of the wafer surface in each process and to appropriately control the process condition.

Since the height of the micro roughness is as very small as from sub-nanometer order to nanometer order, an AFM (Atomic Force Microscope) is generally used and 3D coordinates are measured. However, since the AFM takes a long time for measurement, it is substantially impossible to measure the entire wafer surface.

On the other hand, it is known in the past that the micro roughness is correlated with light scattering. A micro roughness measuring apparatus using light scattering is disclosed in, for example, U.S. Pat. No. 7,286,218 (PTL 5).

As other related art, PTLs 1 to 4, 6 and 7 can be mentioned.

CITATION LIST

Patent Literature

PTL 1: JP-T-9-503299
PTL 2: JP-A-7-333164
PTL 3: JP-A-2010-223770
PTL 4: JP-T-2007-500881
PTL 5: U.S. Pat. No. 7,286,218
PTL 6: U.S. Pat. No. 5,428,442
PTL 7: JP-A-2008-278515

SUMMARY OF INVENTION

Technical Problem

In PTL 5, a detection space of a detection optical system is correlated with a spatial frequency region of micro roughness, and micro roughness evaluation is possible in each spatial frequency region. However, since the number of spatial frequency regions is equal to the number (six in an embodiment) of detection optical systems, consideration is not given to the point that the step size of the spatial frequency is rough.

Besides, although the spatial distribution of scattered light changes in various directions such as forward/backward/sideways according to the difference in micro roughness, consideration is not given to the change of information which does not enter the detection space.

Besides, a step-terrace structure appearing on an epitaxial growth wafer has a sharp peak at a specific spatial frequency in a specific direction. Thus, the intensity of scattered light due to the step-terrace structure has a peak in a specific narrow direction. In the related art, consideration is not given to the point that the peak is buried in the scattered light intensity due to spatial frequency components in the vicinity.

An object of the invention is to provide a highly accurate surface shape measuring apparatus capable of measuring various micro roughness of the entire wafer surface and a method thereof.

Solution to Problems

The invention has a feature that a spatial frequency spectrum relating to a surface shape is continuously obtained.

According to the invention, in a surface shape measuring apparatus which illuminates light to a surface of a sample, detects scattered light from the sample surface by plural detection optical systems, and measures a shape of the sample surface from the plural detection signals, directions of optical axes of the detection optical systems are different from each other, and a process of calculating a spatial frequency spectrum of the sample surface is included.

According to the invention, the illumination light is a spot beam, and the illumination light scans the sample surface by rotation movement and linear movement of the sample.

According to the invention, optical axes of at least two of the detection optical systems are in a plane parallel to a plane of incidence.

According to the invention, optical axes of at least two of the detection optical systems are in a plane parallel to a plane of incidence, and optical axes of at least two of the detection optical systems are in a plane perpendicular to the plane of incidence.

The invention includes a process in which a relation between a spatial frequency spectrum of an already-known surface shape and a detection signal is previously stored in a library, the detection signal from the sample surface is compared with the library, and a spatial frequency spectrum of the sample surface is calculated.

The invention includes a process of calculating a sum of all the detection signals of the detectors and a process of calculating a ratio (signal ratio) of each of the detection signals to the sum of the detection signals.

The invention includes a process of calculating a specific feature quantity of the sample surface by using the spatial frequency spectrum, and a map of the feature quantity of the entire sample surface or a specific region is outputted.

According to the invention, the feature quantity is at least one of a surface roughness in a specific spatial frequency region, a cut-off spatial frequency or a peak spatial frequency of the spatial frequency spectrum, and a thickness of a film forming the sample surface.

The invention includes a process of calculating a height of the sample surface by using the spatial frequency spectrum at a specific position of the sample surface, and a 3D shape at the specific position is outputted.

According to the invention, in a surface shape measuring method in which light is illuminated to a surface of a sample, scattered light from the sample surface is detected by plural detection optical systems, and a shape of the sample surface is measured from the plural detection signals, directions of optical axes of the detection optical systems are different from each other, and a process of calculating a spatial frequency spectrum of the sample surface is included.

Advantageous Effects of Invention

According to the invention, a more detailed surface shape than the related art can be obtained.

DESCRIPTION OF EMBODIMENTS

Hereinafter, a description will be made by using the drawings.

Embodiment 1

As an embodiment of the invention, a surface shape measuring apparatus of micro roughness of a wafer surface in semiconductor device manufacture will be described.

Figure 1:
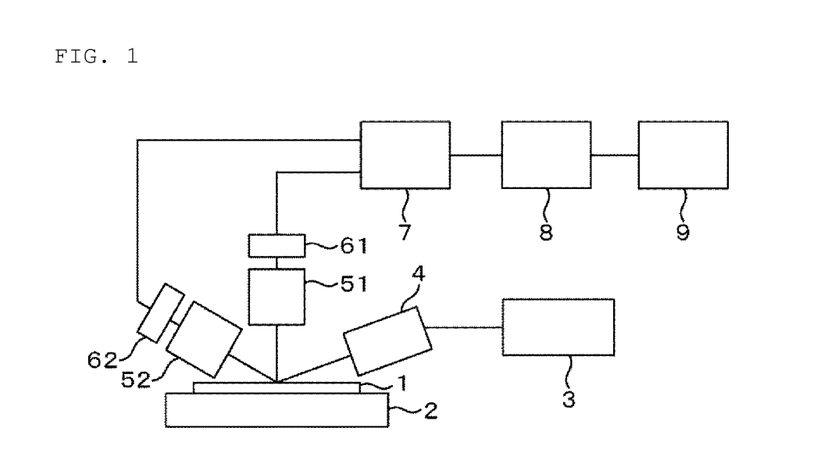
FIG. 1 is a view showing a structure of a surface shape measuring apparatus of embodiment 1.

FIG. 1 shows a rough structure of the surface shape measuring apparatus. Main components include a stage 2 on which a wafer 1 is mounted, a light source 3, an illumination optical system 4 including a lens, a mirror and the like, detection optical systems 51 to 55 (53 to 55 are not shown) including a lens, a mirror and the like, optical detectors 61 to 65 (63 to 65 are not shown), a signal processing system 7, a control system 8 and an operation system 9.

Figure 2:
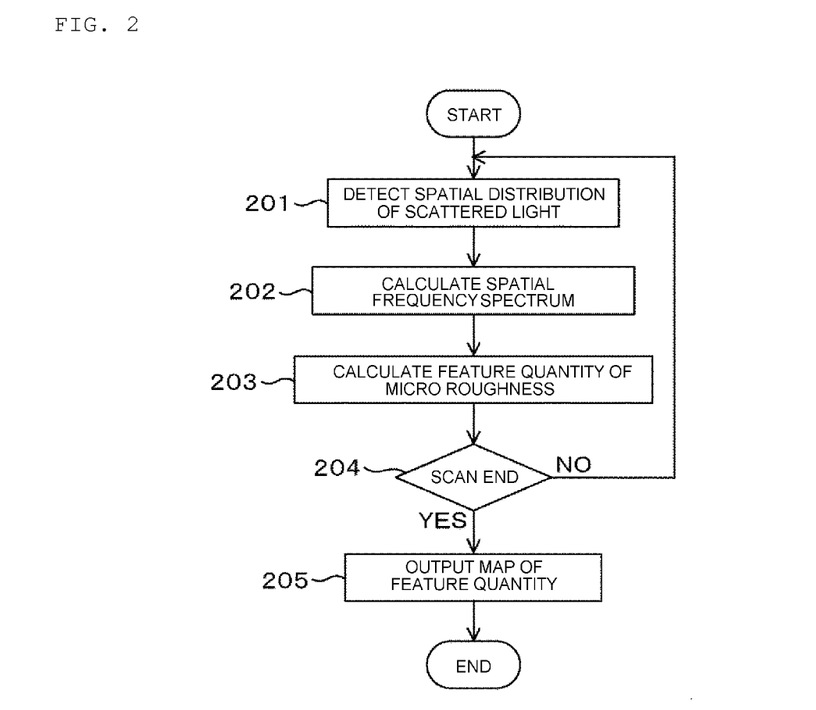
FIG. 2 is a view showing a flow of surface shape measurement of embodiment 1.

Next, a measurement flow of a surface shape in this embodiment will be described by using FIG. 2.

Light of a specific wavelength emitted from the light source 3 is converted into specific polarization light by a polarization filter (not shown). A spot beam with a specific size is formed by the illumination optical system 4, and is illuminated to the wafer 1 at a specific incidence angle. Since micro roughness exists on the wafer surface, scattered light diverges. The detection optical systems 51 to 55 concentrate the scattered light on the optical detectors 61 to 65, respectively. Since the directions of the optical axes of the detection optical systems are different from each other, a set of detection signals reflects the spatial distribution of the scattered light intensity. That is, in the surface shape measuring apparatus of this embodiment, the spatial distribution of the scattered light can be obtained (201 of FIG. 2). Incidentally, the detection optical systems are arranged so that specular light from the wafer surface is not detected. The detection signal is converted into a digital signal by an AD convertor (not shown) and is transmitted to the signal processing system 7.

A storage media storing a library is inside the signal processing system 7, and with respect to a lot of already-known micro roughness, a relation between spatial frequency spectrum and detection signals under the optical condition is recorded. Here, the spatial frequency spectrum is such that when the surface shape is represented by 3D coordinates (X, Y, Z), a 2D Fourier transform is performed on the height Z with respect to (X, Y), and the amplitude is squared. The transmitted detection signals are compared with the detection signals of the library, and the most similar spatial frequency spectrum is calculated (202 of FIG. 2). The calculation of the spatial frequency spectrum will be described later. The spatial frequency spectrum obtained in this way is continuous as in FIG. 3, FIG. 6 and FIG. 10 described later. Next, a feature quantity of the micro roughness is calculated by using the spatial frequency spectrum (203 of FIG. 2) and is transmitted to the control system 8. Incidentally, the calculation of the feature quantity will be described later.

As stated above, the stage is moved so that the spot beam scans the entire wafer surface or a specific region while the micro roughness is locally measured. After the scanning of the entire wafer surface or the specific region is ended (204 of FIG. 2), a map of the feature quantity is displayed on the operation system 9 (205 of FIG. 2). FIG. 2 shows the flow of the above micro roughness measurement.

As the light source 3 of this embodiment, a single wavelength light source such as a laser or a light-emitting diode in a visible light region, an ultraviolet light region and a far-ultraviolet light region can be used. Besides, a continuous wavelength light source such as a mercury lamp or a xenon lamp may be used. In this case, a suitable single wavelength light can be selected by a wavelength filter according to the sample surface.

Besides, as the polarization light of the illumination light of this embodiment, linear polarization light such as s-polarization light or p-polarization light, circularly polarization light, or elliptically polarization light can be selected. The size of the spot beam can be selected according to the spatial resolution of the outputted feature quantity. With respect to the incidence angle of the illumination light, grazing incidence or normal incidence can be selected.

Besides, as the detection optical systems 51 to 55 of this embodiment, a refractive type including a lens, a reflective type including a mirror, a catadioptric type using a combination of a mirror and a lens, and a diffractive type such as a Fresnel zone plate can be used.

Besides, as the optical detectors 61 to 65, a photomultiplier, a multi-pixel photon counter, an avalanche photodiode array and the like can be used.

Besides, the library of this embodiment can be created by using a test wafer. The test wafer is formed by intentionally changing the process condition in the process such as polishing, cleaning, film formation and heat treatment. The micro roughness is measured at sampling positions of the test wafer surface by using an AFM, and the spatial frequency spectrum of the surface shape is calculated. Then, the test wafer is mounted on the surface shape measuring apparatus of this embodiment, and optical detection signals are acquired at the sampling positions. As stated above, with respect to the already-known micro roughness, the relation between the spatial frequency spectrum of the surface shape and the optical detection signals can be recorded. Besides, the spatial frequency spectrum is used, and the detection signals can be predicted by numerical simulation. The spatial frequency spectrum, the refractive index of the surface material, and the illumination condition are made input data, and the spatial distribution of the scattered light is calculated by using a BRDF method (Bidirectional Reflectance Distribution Function). Then, the intensity of the scattered light concentrated by the detection optical system, that is, the detection signal can be predicted by using the spatial distribution of the scattered light.

Besides, as the stage 2 of this embodiment, the combination of rotation movement and linear movement, or the combination of linear movements orthogonal to each other is possible.

Figure 3:
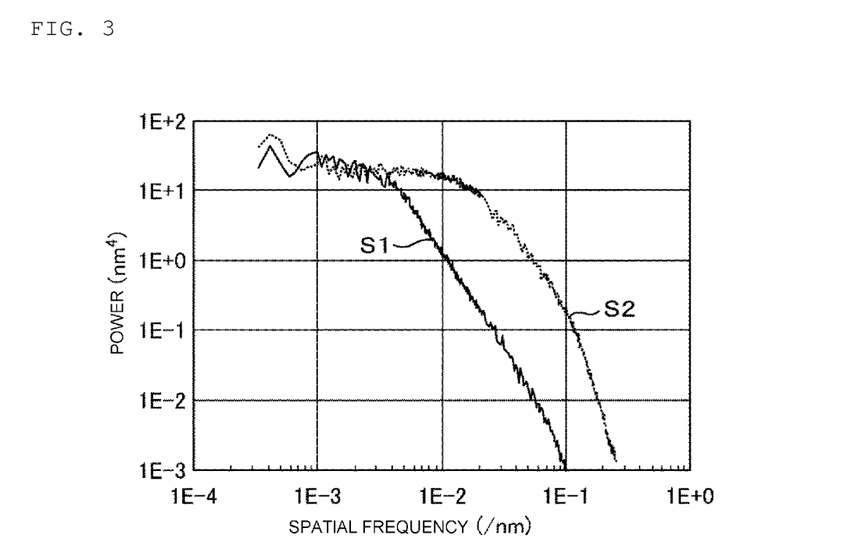
FIG. 3 is a view showing an example of a spatial frequency spectrum of micro roughness.

Next, description will be made on that the measurement accuracy of micro roughness is improved by the measuring apparatus of the invention. In general, the micro roughness is a set of roughness at various spatial frequencies, and the spatial frequency spectrum represents the magnitude of the roughness at each spatial frequency. FIG. 3 shows two spatial frequency spectra S1 and S2 corresponding to the difference of the process condition. In the spatial frequency spectrum S2, the roughness exists in a higher spatial frequency region as compared with the spatial frequency spectrum S1.

Figure 4:
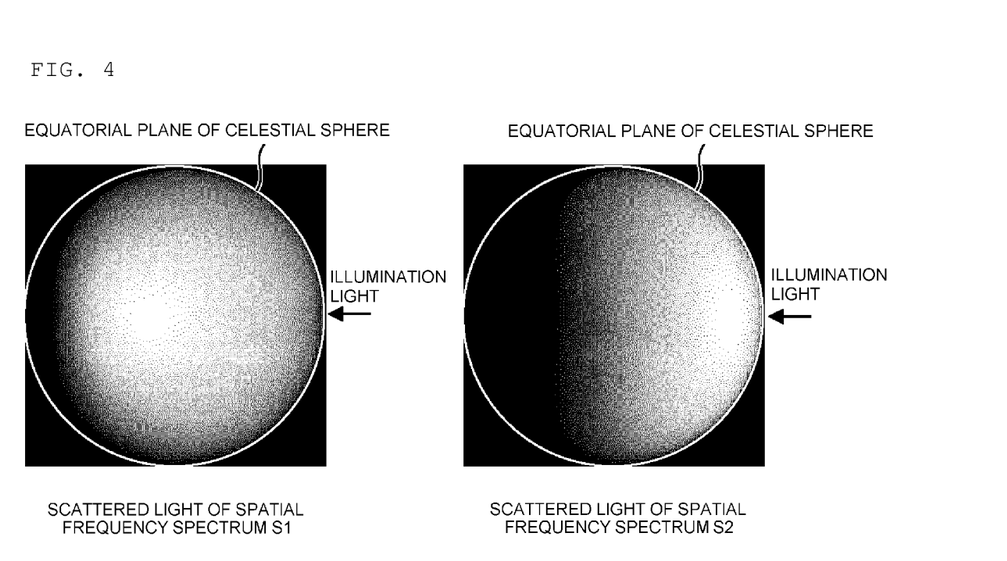
FIG. 4 is a view showing an example of a spatial distribution of scattered light by micro roughness.

FIG. 4 shows the spatial distributions of scattered light intensity due to the micro roughness corresponding to the spatial frequency spectra S1 and S2 (distribution on the celestial sphere is projected on the plane parallel to the wafer surface). It is understood that as compared with the spatial frequency spectrum S1, in the spatial frequency spectrum S2, the region of high scattered light is closer to the rear in the direction of illumination light. That is, when the spatial frequency spectrum of the micro roughness is changed, the region of high scattered light moves in the direction parallel to the plane of incidence (plane including the normal line of the surface of the wafer 1 and the main light beam of the illumination light).

Figure 5:
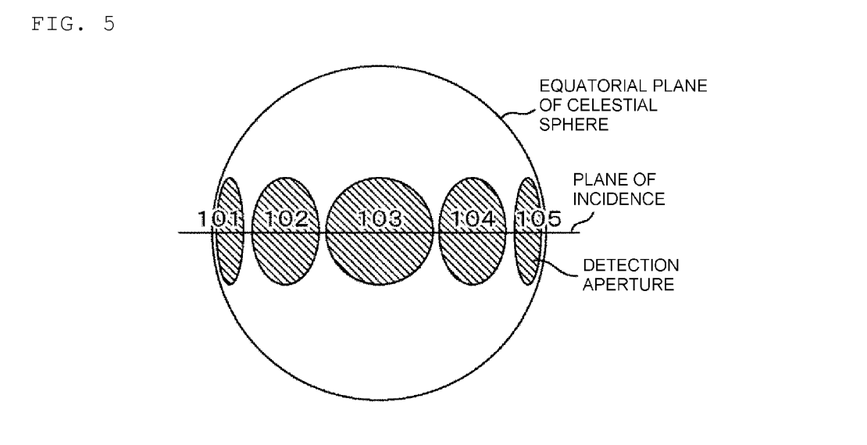
FIG. 5 is a view showing an arrangement of detection optical systems of embodiment 1.

In order to detect the change of the scattered light distribution, the detection optical systems 51 to 55 of this embodiment are arranged as in FIG. 5. FIG. 5 shows an example of the arrangement of the detection optical systems of this embodiment (in FIG. 5, the aperture on the celestial sphere is projected on the surface of the wafer 1). The centers of respective detection apertures 101 to 105 of the detection optical systems 51 to 55, that is, the optical axes of the detection optical systems are in the plane of incidence. In other representation, this can be represented such that the projection line of the plane of incidence to the wafer 1 passes through the projection images of the detection apertures 101 to 105 projected on the wafer 1. By the arrangement as stated above, when the region of high scattered light moves in the direction parallel to the plane of incidence, the change of the scattered light distribution can be sensitively detected. As a result, the change of the spatial frequency spectrum can be sensitively grasped, and the measurement accuracy of the micro roughness is improved.

Next, the calculation of the spatial frequency spectrum of the micro roughness will be described. In general, the spatial frequency spectrum of the micro roughness can be usually fitted by a function including some parameters. A typical fitting function is an ABC-type function of expression (1).

$$P = A/(1+(Bf)^2)^{C/2} \quad (1)$$

Figure 6:
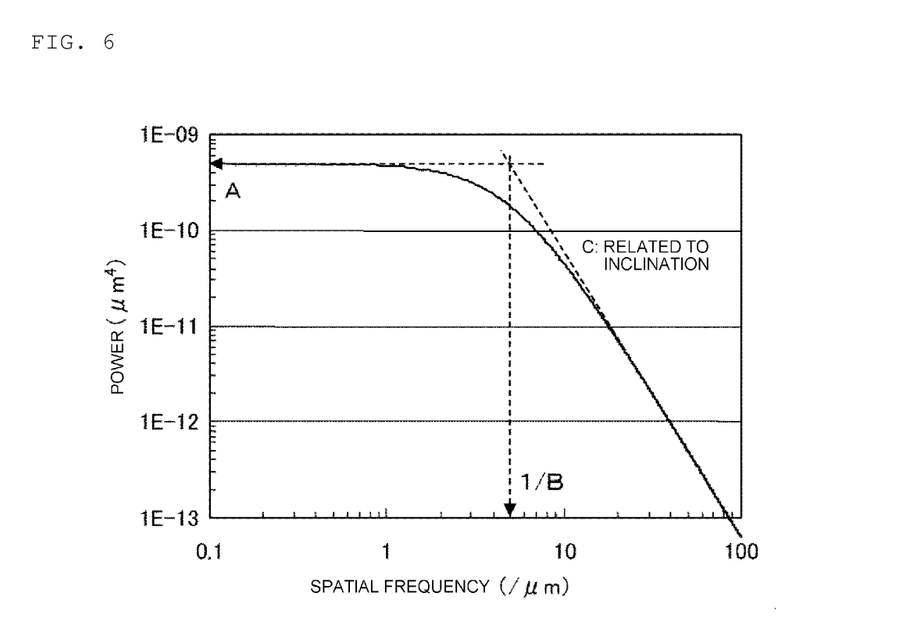
FIG. 6 is a view showing a spatial frequency spectrum of an ABC type function.

Here, P denotes power, f denotes spatial frequency, A denotes power at low spatial frequency side, B denotes cut-off, and C relates to inclination of spectrum. FIG. 6 shows the spatial frequency spectrum of the ABC-type function. The calculation of the spatial frequency spectrum is to obtain the parameters A, B and C.

Figure 7:
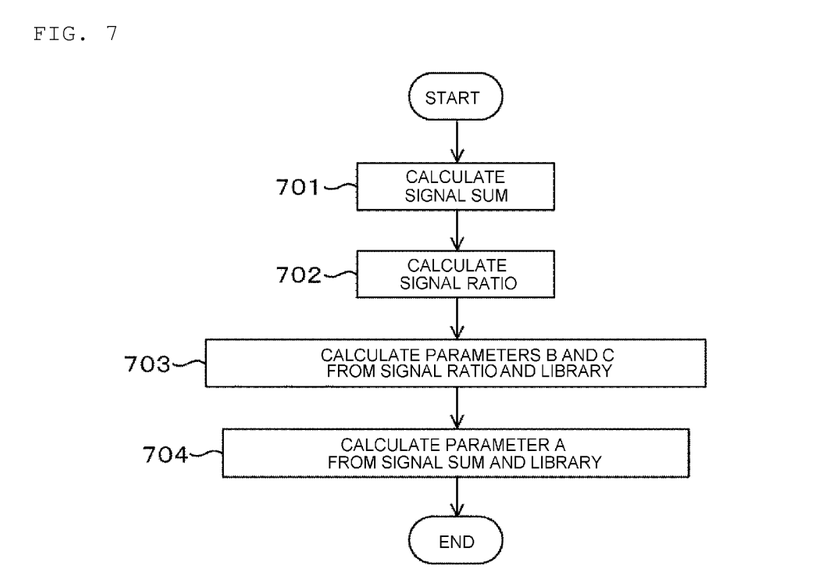
FIG. 7 is a view showing a flow of calculating the spatial frequency spectrum of the ABC type function.

FIG. 7 shows a calculation flow of the spatial frequency spectrum of the ABC-type function. First, the sum of all detection signals of the detectors is calculated (701). Next, the ratio of each of the detection signals to the sum of the detection signals, that is, the signal ratio is calculated (702). The signal ratio is compared with the signal ratio library, and the parameters B and C are calculated (703). Finally, the parameters B and C and the signal sum are compared with the signal sum library, and the parameter A is calculated (704). The above-mentioned calculation of the parameters can be performed by numerical calculation such as a least square method. As stated above, when the spatial frequency spectrum is represented by the parameters, the data capacity can be compressed, and accordingly, the spatial frequency spectrum data of all measurement positions can be stored.

Figure 8:
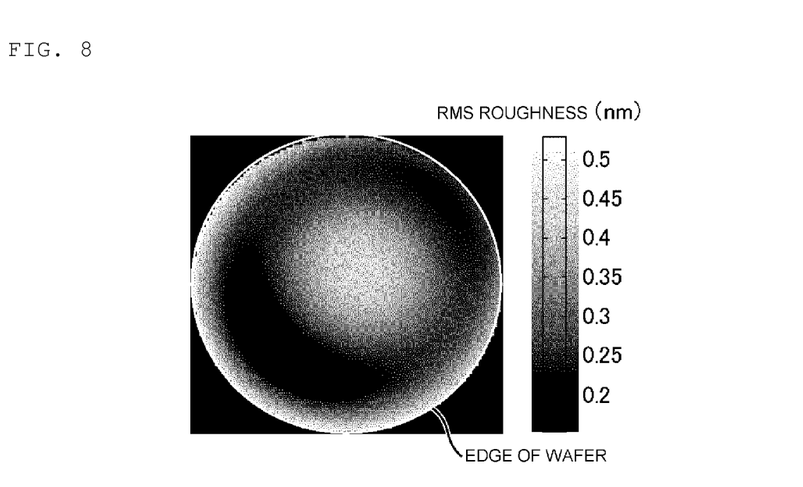
FIG. 8 is a view showing an example of a map of RMS roughness of the entire wafer surface.

Next, the calculation and output of the feature quantity of the micro roughness will be described. An operator selects a noteworthy feature quantity according to a process. The feature quantity is, for example, RMS roughness in a noteworthy spatial frequency region, cut-off spatial frequency of the spatial frequency spectrum, peak spatial frequency or the like. The RMS roughness is calculated by integrating the spatial frequency spectrum in the spatial frequency region. In this embodiment, since the spatial frequency spectrum is calculated as the continuous function of the spatial frequency, the spatial frequency region can be arbitrarily set. FIG. 8 shows an example of a map of the RMS roughness of the entire wafer surface. Whether the process condition is adequate or not can be determined by the map of the RMS roughness. Besides, the cut-off spatial frequency and the peak spatial frequency are calculated by the analysis of the spatial frequency spectrum. In this embodiment, since the spatial frequency spectrum is calculated as the continuous function of the spatial frequency, the analysis can be performed at high spatial frequency resolution. The height of the roughness in the spatial frequency region is determined by the map of the cut-off spatial frequency. Besides, whether or not micro roughness in a specific direction and at a specific spatial frequency, such as a step-terrace structure, exists is turned out by the map of the peak spatial frequency.

Figure 9:
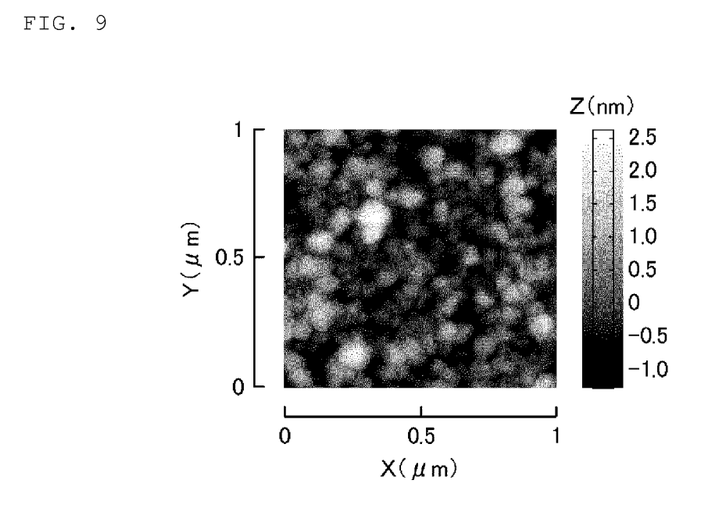
FIG. 9 is a view showing an example of a 3D shape of micro roughness.

Next, the calculation and output of 3D shape of micro roughness will be described. The operator refers to the map of the feature quantity, and specifies a noteworthy position on the wafer. Besides, the operator specifies a noteworthy spatial frequency region. The signal processing system uses the spatial frequency spectrum at the position, and performs a Fourier inverse transform in the spatial frequency region to calculate the 3D shape and the coordinates (X, Y, Z) of the 3D shape. In this embodiment, since the spatial frequency spectrum is calculated as the continuous function of the spatial frequency, the spatial frequency region can be arbitrarily set. The coordinate data is transmitted to the operation system, and the 3D shape at the specified position is displayed. FIG. 9 shows an example of the 3D shape of the wafer surface. The operator can visually recognize the micro roughness by such a display.

Here, although the 3D shape includes, for example, the particle size of the surface, the phase of the particle size of the surface is random. Then, when the 3D shape is obtained, a random number is generated and a Fourier inverse transform can be performed. The Fourier inverse transform using the random number will be described in more detail. When the Fourier inverse transform using the random number is performed, the following flow is used.

(1) The square root of power spectrum is taken and is made an amplitude A.

(2) A phase φ is generated by the random number.

(3) A complex amplitude A*(cos φ+i*sin φ) is subjected to the Fourier inverse transform.

Incidentally, the wafer surface may have a single layer structure or a multi-layer structure. When the multi-layer structure is adopted and the upper layer is transparent, the micro roughness of an interface between the upper layer and the lower layer can also be measured. Besides, when the multi-layer structure is adopted and the upper layer is transparent, the film thickness of the upper layer can also be measured.

Embodiment 2

Next, embodiment 2 will be described. According to embodiment 2, measurement accuracy is improved also in anisotropic micro roughness. In embodiment 2, portions different from embodiment 1 will be mainly described.

Figure 10:
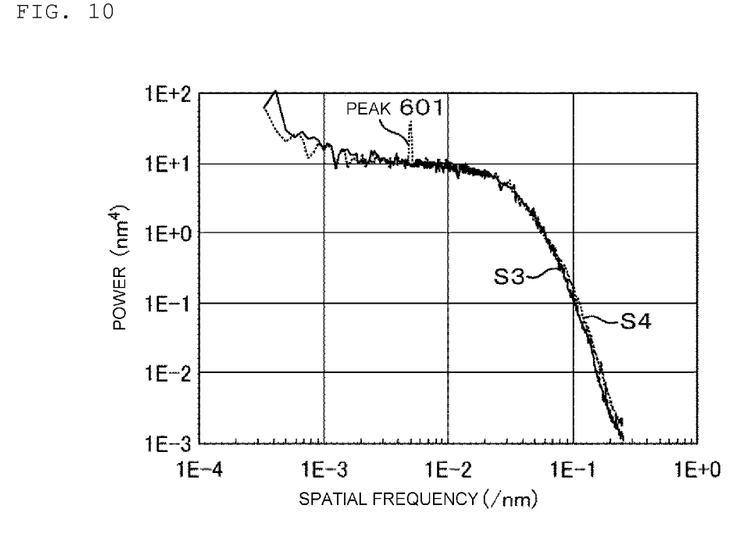
FIG. 10 is a view showing an example of a spatial frequency spectrum of anisotropic micro roughness.

A step-terrace structure appearing in an epitaxial growth wafer has a specific spatial frequency in a specific direction. FIG. 10 shows two spatial frequency spectra S3 and S4 of the micro roughness of the epitaxial growth wafer. The spatial frequency spectrum S3 is in a direction in which the step-terrace structure does not appear, and the spatial frequency spectrum S4 is in a direction in which the step-terrace structure appears. In the step-terrace structure, the spatial frequency spectrum has a sharp peculiar peak 601 at a specific spatial frequency in a specific direction. The peak 601 corresponds to the step-terrace structure.

Figure 11:
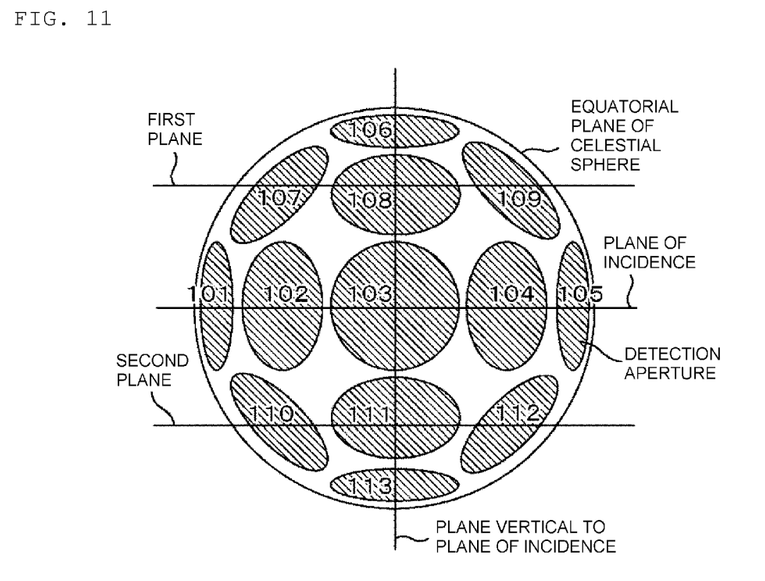
FIG. 11 is a view for explaining embodiment 2.

FIG. 11 shows an example of a detection optical system arrangement suitable for detecting the spatial distribution of scattered light due to such anisotropic micro roughness (aperture on the celestial sphere is projected on a plane parallel to a wafer surface). That is, the surface shape measuring apparatus of this embodiment 2 includes thirteen detection optical systems, and thirteen optical detectors corresponding thereto. Detection apertures 101 to 113 of FIG. 11 are respectively detection apertures of the thirteen detection optical systems.

The centers of the detection apertures 101 to 105 of embodiment 2, that is, the optical axes of the detection optical systems are in the plane of incidence. Besides, the centers of the detection apertures 107 and 109, and the centers of the detection apertures 110 and 112 are respectively on planes parallel to the plane of incidence. Besides, the centers of the detection apertures 103, 106, 108, 111 and 113 are in a plane perpendicular to the plane of incidence. Besides, the centers of the detection apertures 107 and 110, and the centers of the detection apertures 109 and 112 are respectively on planes perpendicular to the plane of incidence.

In other words, it can be expressed that the centers of the detection apertures 101 to 105 are in the plane of incidence of the illumination optical system, the center of the detection aperture 101 and the center of the detection aperture 105 are symmetric with respect to the plane perpendicular to the plane of incidence, and the center of the detection aperture 102 and the center of the detection aperture 104 are symmetric with respect to the plane perpendicular to the plane of incidence. Besides, it can also be expressed that the center of the detection aperture 106 and the center of the detection aperture 113 are in the plane perpendicular to the plane of incidence and are symmetric with respect to the plane of incidence. Besides, the center of the detection aperture 108 and the center of the detection aperture 111 are in the plane perpendicular to the plane of incidence and are symmetric with respect to the plane of incidence. Further, it can be expressed that the center of the detection aperture 107 and the center of the detection aperture 109 are in a first plane parallel to the plane of incidence and are symmetric with respect to the perpendicular plane. Further, it can be expressed that the center of the detection aperture 110 and the center of the detection aperture 112 are in a second plane parallel to the plane of incidence and are symmetric with respect to the perpendicular plane. And it can be expressed that the first plane and the second plane are symmetric with respect to the plane of incidence.

By the detection optical system arrangement as stated above, the change of scattered light distribution in various directions can be sensitively grasped. As a result, the change of spatial frequency spectrum in various directions can be sensitively grasped, and the measurement accuracy of the anisotropic micro roughness is improved.

Embodiment 3

Next, embodiment 3 will be described. In embodiment 3, spatial frequency resolution is further improved in embodiment 1 and embodiment 2.

Figure 12:
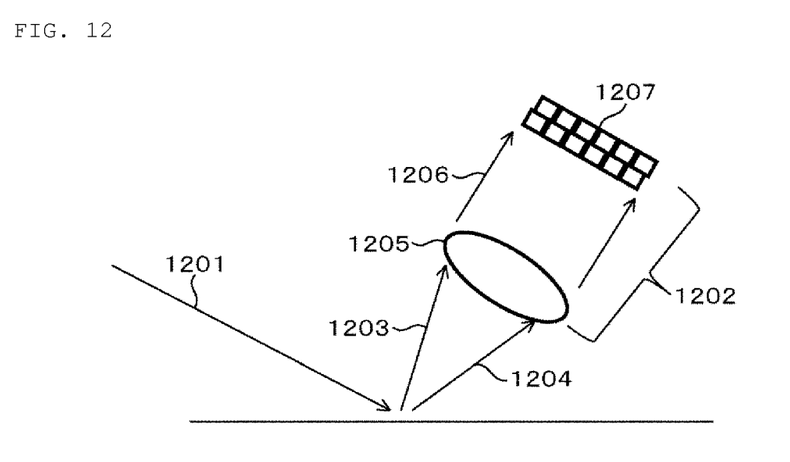
FIG. 12 is a view for explaining embodiment 3.

A point in which a light 1201 is illuminated to a surface of a wafer 1 is the same as embodiment 1 and embodiment 2. In embodiment 3, the detection optical system of embodiment 1 and embodiment 2 is replaced by a Fourier transform optical system 1202. The Fourier transform optical system 1202 detects by using a Fourier transform lens 1205 to concentrate scattered lights 1203 and 1204 from the wafer 1, and a 2D sensor 1207 to detect a parallel light 1206 collimated by the Fourier transform lens 1205. As the 2D sensor, a charge coupled device (CCD), a time delay integration sensor (TDI), a multi-pixel photon counter, an avalanche photodiode array or the like can be used.

In embodiment 3, after the light is detected by the 2D sensor 1207, the same process as embodiments 1 and 2 is performed.

In embodiment 3, since the intensity distribution of scattered light incident on the detection optical system can be detected, the spatial frequency resolution can be further improved. Thus, a sharp peak in a specific direction, such as the scattered light of the step-terrace structure, is effectively detected.

According to the measuring apparatus of the invention, the micro roughness of the entire wafer surface is measured at high accuracy in each of semiconductor manufacture processes, and the process condition can be appropriately controlled.

Besides, the measuring apparatus of the invention can be widely applied also to the measurement of micro roughness of a magnetic storage media or the like.

REFERENCE SIGNS LIST 1 wafer
2 stage
3 light source
4 illumination optical system
7 signal processing system
8 control system
9 operation system
51 to 55 detection optical system
61 to 65 optical detector

The invention claimed is:

1. A surface shape measuring apparatus for obtaining a surface shape of a sample, comprising:

an illumination optical system to illuminate light to the sample, the illumination optical system including a light source and optics, the optics being configured to direct light from the light source to the sample;

a plurality of detection optical systems to detect scattered light from the sample and to output a detection signal corresponding to the detected scattered light, each of the plurality optical systems including a detector and an AD convertor;

a storage medium which stores a library; and a digital signal processing part which obtains a continuous spatial frequency spectrum of micro roughness of the sample by using detection signals of the plurality of detection optical systems and the library.

2. The surface shape measuring apparatus according to claim 1, wherein the library records a relation between a spatial frequency spectrum of a surface shape and an optical detection signal with respect to an already-known micro roughness.

3. The surface shape measuring apparatus according to claim 1, wherein optical axes of the plurality of detection optical systems are in a plane of incidence of the sample.

4. The surface shape measuring apparatus according to claim 1, wherein the digital signal processing part obtains a ratio of a sum of detection signals of the plurality of detection optical systems and one detection signal, and obtains the spatial frequency spectrum by using the ratio and the library.

5. The surface shape measuring apparatus according to claim 1, wherein a center of a first detection aperture of the plurality of detection optical systems and a center of a second detection aperture are in a plane of incidence of the illumination optical system and are symmetric with respect to a plane perpendicular to the plane of incidence, a center of a third detection aperture of the plurality of detection optical systems and a center of a fourth detection aperture are in the perpendicular plane and are symmetric with respect to the plane of incidence, a center of a fifth detection aperture of the plurality of detection optical systems and a center of a sixth detection aperture are in a first plane parallel to the plane of incidence and are symmetric with respect to the perpendicular surface, and a center of a seventh detection aperture of the plurality of detection optical systems and a center of an eighth detection aperture are in a second plane parallel to the plane of incidence and are symmetric with respect to the perpendicular surface, and the first plane and the second plane are symmetric with respect to the plane of incidence.

6. The surface shape measuring apparatus according to claim 1, wherein the plurality of detection optical systems include a Fourier transform optical system.

7. The surface shape measuring apparatus according to claim 1, wherein the digital signal processing part obtains at least one of a surface roughness in a spatial frequency region in the spatial frequency spectrum of micro roughness, a cut-off spatial frequency of the spatial frequency spectrum of micro roughness, and a peak spatial frequency.

8. The surface shape measuring apparatus according to claim 1, wherein the digital signal processing part performs a Fourier inverse transform on the spatial frequency spectrum of micro roughness of the sample.

9. The surface shape measuring apparatus according to claim 8, wherein the digital signal processing part uses a random number to perform the Fourier inverse transform.

10. The surface shape measuring apparatus according to claim 1, wherein the continuous spatial frequency spectrum is expressed by a plurality of parameters.

11. The surface shape measuring apparatus according to claim 10, wherein the continuous spatial frequency spectrum is ABC type function, wherein the A denotes power at low spatial frequency side, B denotes cut-off, C relates to inclination of spectrum.

12. The surface shape measuring apparatus according to claim 1, wherein the detection optical systems are arranged so as to capture displacement of a region of high scattered light in a direction parallel to a plane of incidence.

13. The surface shape measuring apparatus according to claim 1, wherein the digital signal processing part obtains at least one of a surface roughness in a spatial frequency region in the spatial frequency spectrum of micro roughness, a cut-off spatial frequency of the spatial frequency spectrum of micro roughness, and a peak spatial frequency.

* * * * *